United States Patent [19]

Lai

[11] Patent Number: 4,466,915

[45] Date of Patent: Aug. 21, 1984

[54] NON-CATALYTIC KETOFORM SYNTHESES

[75] Inventor: John T. Lai, Broadview Heights, Ohio

[73] Assignee: The B. F. Goodrich Company, Akron, Ohio

[21] Appl. No.: 427,371

[22] Filed: Sep. 29, 1982

[51] Int. Cl.³ .................... C07D 243/08; C10M 1/32; C10M 1/24
[52] U.S. Cl. .............................. 260/239.3 R; 544/384; 544/354; 544/344; 562/567; 564/197; 564/164; 564/193; 546/223
[58] Field of Search ................. 260/239.3 R; 544/384, 544/354; 562/567; 564/164, 197; 546/223

[56] References Cited

U.S. PATENT DOCUMENTS 4,167,512 9/1979 Lai ........................................ 544/384
4,310,429 1/1982 Lai ........................................ 564/164

Primary Examiner—Robert T. Bond
Attorney, Agent, or Firm—Alfred D. Lobo; Nestor W. Shust; Alan A. Csontos

[57] ABSTRACT

A known base-induced catalytic ketoform synthesis can now be carried out without sacrificing the directivity of the prior art process, but non-catalytically, that is, in the absence of the phase transfer catalyst heretofore required, provided the ketone/araldehyde is present in large excess from about 2 to about 25 times the calculated molar amount necessary to yield the reaction product. This synthesis obviates the problems of separating and recovering a phase transfer catalyst used in the prior art process.

11 Claims, No Drawings

NON-CATALYTIC KETOFORM SYNTHESES

BACKGROUND OF THE INVENTION

It is known in the prior art that the 'ketoform synthesis' is highly effective in the synthesis of compounds which are otherwise difficult, if not impossible to synthesize. The 'ketoform synthesis' is so called because a saturated or unsaturated monoketone ("ketone"), or, an aromatic monoaldehyde ("araldehyde"), and a haloform are reacted in the presence of a phase transfer catalyst, an organic solvent and aqueous or solid alkali, with a 'starting' compound (referred to herein as the "reactant" compound), to yield various reaction products, the reaction being "base-induced". The structure of the reaction product depends upon the regioselectivity of the reaction with respect to particular portions of the structure of the reactant compound. Because the prior art ketoform synthesis was carried out in the presence of a phase transfer catalyst, it is referred to herein as the "catalytic ketoform synthesis".

It was hypothesized in the prior art reaction, that the presence of the phase transfer catalyst along with substantially equimolar quantities of ketone or aldehyde and haloform, was somehow responsible in this base-induced reaction, for avoiding side reactions which might form unwanted by-products such as isonitrile, formamide and alpha-chloro acids, inter alia. It has now been found that the formation of such unwanted by-products is also avoided in the absence of the phase transfer catalyst, and a large excess of ketone, or araldehyde provided it (ketone/araldehyde) is a solvent for the reactant compound.

The catalytic ketoform synthesis is disclosed in U.S. Pat. Nos. 4,167,512; 4,297,497; and 4,298,737 to produce stabilizers for organic materials which are sensitive to ultraviolet light (referred to as u-v light stabilizers), and lubricity additives particularly in functional fluids. The disclosures of the foregoing patents are incorporated by reference thereto as if fully set forth herein. Briefly, either an acyclic or cyclic ketone, typically acetone, or an araldehyde, typically benzaldehyde (optionally substituted), and chloroform are each necessary reactants in the synthesis. In addition, at least one of them, that is, either the ketone/araldehyde or the haloform, is a solvent for the reactant compound, so that the ketone/araldehyde, the haloform and the solution of the reactant compound are all present in a nonaqueous phase. Also present is an aqueous phase and alkali, typically NaOH in solution.

For example, in U.S. Pat. No. 4,167,512 it was shown that polysubstituted 2-keto-1,4-diazacycloalkanes are easily synthesized from readily available starting materials, using the catalytic ketoform synthesis. Particularly, 1,2-diamines or 1,3-diamines are converted to the aforesaid polysubstituted cyclic compounds at room temperature and atmospheric pressure in the presence of an onium salt phase transfer catalyst.

U.S. Pat. No. 4,297,497 teaches the preparation of $N^1,N^4$-dimethyl-3,3-dimethyl-2-piperazinone by the catalytic ketoform synthesis using N,N'-dimethyl-ethylene diamine as the reactant compound either with BTAC or a phosphonium salt.

U.S. Pat. No. 4,298,737 teaches the preparation of piperidinyl substituted 1,4-diaza-2-cycloalkanones by a catalytic ketoform synthesis in which the reactant compound is a N-piperidinyl substituted diamine such as 4-(3-amino-1,3-dimethyl-butylamino)-2,2,6,6-tetramethylpiperidine.

A more detailed discussion of the base-induced catalytic ketoform synthesis will be found in "Hindered Amines. Synthesis of Hindered Acyclic -Aminoacetamides" by Lai, John T., *J. Org. Chem.*, 45, 3671–3 (1980). Despite the effectiveness of the phase transfer catalyst in the ketoform synthesis, the synthesis is burdened with the cost of separating and recovering the expensive phase transfer catalyst. Simply separating the catalyst from the reaction mass often presents more of a problem than is economically tolerable, with the result that otherwise highly useful and desirable compounds never find their way to the marketplace. Moreover, this catalytic ketoform synthesis was only known to be useful in the formation of cyclized reaction products; now it may be used for the formation of acyclic reaction products as well.

The logical approach to solve the problem was to devise several ways of trying to separate the catalyst from the reaction mass, and/or ways to confine the catalyst in the reaction zone so that separation and recovery of the catalyst would be a more manageable problem. Neither approach appreciably alleviated the economic burden of having to separate and recover the catalyst.

Quite by chance, it transpired that the most economical way to solve the problem of separating and recovering catalyst was to avoid using the catalyst in the first place. Thus, it is to this catalyst-free (hence termed "non-catalytic") ketoform synthesis, to which this invention is directed.

A long time ago, the influence of substituents in the $C_6H_6$ nucleus on the formation of aromatic isonitriles by the Hoffmann reaction, was studied by the reaction of chloretone (formed by the reaction of chloroform with acetone), aniline and KOH (see "Action of Chloretone and KOH on Primary Aromatic Base" by Banti, G., *Gazz. Chim. Ital.*, 59 819–24, 1929). In the presence of ethanol as a solvent, the reaction product was phenylaminoisobutyric acid anilide. However, it has been found that presence of an alcohol solvent interferes with the directivity of the ketoform synthesis and tends to produce unwanted byproducts in my process, presumably because of the presence of free chloroform and a large excess of ketone. In my ketoform synthesis, if a primary alcohol is present, it is necessarily a reactant.

The problems with directivity and formation of by-products are also thought to derive from the preformation of chloretone which may interfere with the formation of the trichloromethide ion. This trichloromethide ion is deemed essential to the formation of an epoxide intermediate in the ketoform synthesis. (see Lai, J. T. publication, supra). Formation of the epoxide intermediate is thought to occur in a manner analogous to that taught in an article titled "Formation of Dichloro Oxiranes from Ketones under Phase Transfer Conditions" by Greuter, H. et al., in *Helvetica Chimica Acta*, Vol 62 pg 1275–81 Fasc. 4 (1979)-Nr. 131. Thus, the non-catalytic ketoform synthesis of my invention is carried out without the preformation of chloretone and in the absence of alcohol.

SUMMARY OF THE INVENTION

It has been discovered that the known base-induced catalytic ketoform synthesis can now be carried out without sacrificing the directivity of the prior art process, but non-catalytically, that is, in the absence of the phase transfer catalyst heretofore required, provided the ketone/araldehyde is present in large excess from about 2 to about 25 times the calculated molar amount necessary to yield the reaction product.

It is therefore a general object of this invention to provide a non-catalytic ketoform synthesis which obviates the problems of separating and recovering a phase transfer catalyst used in the prior art process.

The non-catalytic ketoform synthesis is particularly effective in the manufacture of cycloalkanones by conversion of the following reactant compounds:

(a) cyclic or acyclic 1,2-diamines, or 1,3-diamines, to polysubstituted 2-keto-1,4-diazacycloalkanes;

(b) N-piperidinyl substituted diamines to piperidinyl substituted 1,4-diaza-2-cycloalkanones; and, (c) N-substituted-N'-substituted-N-alkanediamines such as N-(2-butyl)-N'-(2-amino-2-methylpropyl)-1,2-ethanediamine, to a polysubstituted piperazinone such as 1-[2-(2-butylamino)ethyl]-3,3,5,5-tetramethyl-2-piperazinone.

The non-catalytic ketoform synthesis is also highly effective in the manufacture of certain reaction products in which there is no cyclization to a cycloalkanone, as in the conversion of the following reactant compounds:

(a) primary or secondary amines to alpha-aminoacetamides;

(b) 2,2'-substituted-2-amino-alkanols such as 2-methyl-2-amino-1-propanol, to a polysubstituted alkali metal hydroxy-ethylaminoacetate such as sodium tetramethyl-hydroxyethylaminoacetate; and (c) amino-2,2,6,6-tetrasubstituted-piperidine to polysubstituted alpha-aminoacetamides in which one of the substituents on either the amine N atom, or the amide N atom, or both N atoms, is tetrasubstituted-piperidinyl.

DETAILED DESCRIPTION OF PREFERRED EMBODIMENTS

In this non-catalytic base-induced ketoform synthesis, the reactant compound is an amine nucleophilic agent, whether a primary or a secondary amine, or one of each if desired, which reactant compound is reacted with a saturated or unsaturated monoketone or aromatic monoaldehyde and a haloform to yield a substituted reaction product. An epoxide intermediate is thought to be formed, and the portion of the intermediate attacked by the amine will depend upon the regioselectivity of the reaction under the particular conditions it is carried out. The precise mechanism of the reaction is not fully understood, but a mechanism for the phase transfer catalyzed reaction is hypothesized in the publication "Hindered Amines. etc." supra, and it is assumed to be essentially the same.

Diazacycloalkanones are prepared from cyclic or acyclic 1,2-diamines or 1,3-diamines which may include two primary amine moieties, one primary amine moiety and one secondary amine moiety, or two secondary amine moieties. The amine is chosen to provide the desired substituents at preselected locations in the reactant compound, to provide upon cyclization, the desired number of C atoms in the bridge (between N atoms) on one side of the ring, and also to provide the desired substituents on preselected C atoms of this bridge. It will thus be evident that a straight chain or acyclic diamine will be appropriate where a monocyclo-1,4-diazacycloalkane is to be synthesized, and a cyclic amine will be used when a bicyclo (fused rings, or spiro-) substituted 1,4-diazacycloalkane is to be made.

The presence of a haloform, such as chloroform, or bromoform takes part in the reaction as a necessary reagent, but may also have some function as a catalyst, though the precise mechanism or the manner in which the haloform affects the reaction, is not understood. No catalytic action is ascribed by me to the haloform in this non-catalytic ketoform synthesis. This hypothesis that a haloform is essential is based upon the fact that, when another solvent is substituted for the haloform, the reaction does not proceed.

Since the haloform is a reactant, it is essential that at least an equimolar amount (as the amine) be used if good yields of the reaction product are to be obtained. Lesser amounts of chloroform (say) will yield product, but not in an amount desired. Preferred haloforms are chloroform and bromoform. It is essential that at least a stoichiometric amount of haloform be used if no amine is to be left unreacted. Though a small amount of unreacted amine is not deleterious, it is desirable to employ a slight excess over stoichiometric of the haloform to avoid unreacted amine. Though an excess, up to about a 50% excess over stoichiometric provides acceptable results, more than 50% over stoichiometric is to be avoided because of the formation of undesirable side products.

The monoketone is preferably saturated and may be cyclic or acyclic. Where a 2-keto-1,4-diazacycloalkane is to be formed, useful ketones are those which cyclize forming a fixed two-carbon bridge between the $N^1$ and $N^4$ atoms of the diaza ring. Preferred monoketones are cycloalkanones, dialkylketones and aralkylketones.

Only aromatic monoaldehydes ("araldehydes") appear to be effective in this non-catalytic ketoform synthesis, benzaldehyde and substituted benzaldehydes, being most preferred, particularly where the substituents are lower alkyl having from 1 to about 6 carbon atoms. The particular substituent(s) on the benzaldehyde will affect the rate of the reaction and generally be introduced into the reaction product, but do not otherwise affect the progress of the reaction, though hydrocarbyl substituents are preferred.

The preferred base for inducing the reaction is an aqueous alkali metal hydroxide solution such as aqueous sodium hydroxide, or potassium hydroxide, preferably in the range from about 20 percent to about 70 percent solutions. If the alkali metal hydroxide is used in solid form, it is preferably in finely divided powder form typically less than 80 U.S. Standard mesh in size. The amount used is not critical but at least a trace amount appears to be essential for the progress of the desired reaction. It is preferred to use sufficient aqueous alkali solution to form a visually distinct aqueous phase in the presence of the organic solvent phase. In general, the amount of aqueous alkali used is preferably about three (3) equivalents of the amine. A slight excess over three equivalent is preferable, but a large excess is to be avoided.

Though aqueous alkali is most preferable, water is not an essential requirement for the progress of the synthesis, though it will be appreciated that even where solid alkali metal hydroxide is used, there may be a trace of water associated with it.

Typically, the reactants are mixed in the organic phase, the order being unimportant. The aqueous or solid alkali is then added to the system, with stirring, and heat is removed by cooling since the reaction is generally exothermic. The reaction proceeds at subatmospheric and superatmospheric pressures, and pressure considerations are not critical to the practice of the invention except as the requirements of the system may dictate. Operation at atmospheric is most preferred because there appears to be no substantial advantage to be gained from operating at higher pressures.

The non-catalytic ketoform synthesis, like the prior art synthesis, is of particular interest because it generally proceeds at room temperature or below, at satisfactory speed, and with excellent yields. However, it may be carried out at any temperature within a wide range from about the freexing point of the reaction mass to about the reflux temperature of the ketone/aldehyde or organic solvent, provided the reflux temperature is lower than that which is deleterious to the reaction product formed. The reaction is most preferably carried out at room temperature or below, it being preferred to use as low a temperature as is consistent with obtaining economical rates of reaction, because most of the reactions are exothermic. The reactions are preferably carried out at a temperature in the range from about $-10°$ C. to about 50° C., and most preferably between 0° C. and about 20° C.

If a sufficiently large excess of ketone/araldehyde is used so that the reactant compound and haloform are in solution, no additional solvent may be necessary. Where for example, a large excess of acetone is employed, the addition of a 50% aqueous solution of NaOH will produce a single liquid phase, and the reaction will proceed in this phase. It is not essential that two liquid phases be present, but it is found that the reaction proceeds better if there are two liquid phases. Whether or not there are two liquid phases, NaOH or KOH or other alkali metal hydroxide may be present either as solid or in solution.

Generally it is preferable to use an organic solvent which is essentially inert under the conditions of the reaction, and is immiscible in water, so as to provide a second liquid phase. Most preferred are common aromatic and paraffinic solvent such as benzene, p-xylene, toluene, dichloromethane, chlorobenzene, cyclohexane, particularly those in which the reactant compound is soluble, such as hydrohalomethylenes, particularly hydrochloromethylenes, sulfolane, dibutyl ether, dimethyl sulfone, diisopropyl ether, di-n-propyl ether, 1,4-dioxane, tetrahydrofuran, hexane, carbon tetrachloride and the like. Most preferred solvents are hydrochloromethylenes.

The non-catalytic ketoform synthesis results in cyclization of the amine nucleophilic agent in several embodiments as follows:

Preparation of 2-keto-1,4-diazacycloalkanes:

The 2-keto-1,4-diazacycloalkanes prepared by the non-catalytic ketoform synthesis of this invention have a structure selected from

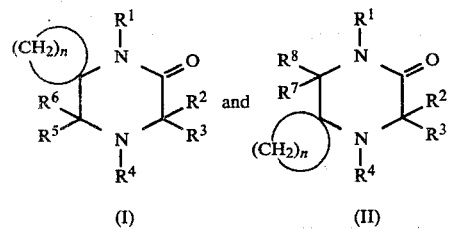

(I)                (II)

wherein, n represents an integer in the range from 0 to about 6; so when n is 0 then (I) and (II) represent substituted 2-keto-piperazine, and when n is 4 and the compound is a bicyclo fused ring structure, then (I) and (II) represent 2-keto-decahydroquinoxaline;

$R^1$ and $R^4$ independently represent hydrogen, alkyl, hydroxyalkyl, haloalkyl, cyanoalkyl, aminoalkyl, alkenyl, aralkyl, and carboalkoxy;

$R^4$ optionally also represents oxygen;

$R^2$ and $R^3$ indenepdently represent alkyl, haloalkyl, cyanoalkyl, cycloalkyl, hydroxy-cycloalkyl, aminoalkyl, and alkenyl; and, $R^5$, $R^6$, $R^7$, $R^8$ independently represent alkyl, haloalkyl, cyanoalkyl, aminoalkyl, alkenyl, and aralkyl, and $R^2$-$R^8$ may in combination, one with another, represent cycloalkyl from 5 to about 14 carbon atoms at least 4 of which are cyclized and optionally containing a keto, ester, amide, ether, thio or hydroxy group.

For example, a primary aliphatic 1,2-diamine with an excess of a ketone and in the presence of an effective amount of chloroform and aqueous base will yield a 1,4-diazacycloalkan-2-one.

By "alkenyl" is meant the same as "alkylene", that is, a bivalent group derived by the removal of one H atom from two different carbon atoms of an alkane, but also includes methylene which, as an exception, is obtained by the removal of two H atoms from the same carbon atom. Examples of short chained alkylene substituents are methylene ($-CH_2-$), ethylene ($-CH_2-CH_2-$), 1,2-propylene ($-CH_3-CH-CH_2-$), 1-3-propylene ($-CH_2-CH_2-CH_2-$), butylene and the like.

In a manner analogous to the foregoing, 1,4-diazacloalkan-2-ones are also formed when the reactant compound is a diamine having one primary and one secondary amine group, and where the chloroform and reactant compound are present in substantially equimolar maounts, at least a two-fold excess of ketone or araldehyde is required.

In an analogous manner, 3,3-pentamethylene-2-quinoxalinone is prepared from o-phenylene diamine, cyclohexanone and $CHCl_3$ in a base-induced reaction.

Analogous results are obtained when benzaldehyde, or p-methlbenzaldehyde is substituted for a ketone used in the foregoing reaction.

Preparation of piperidinyl-substituted 1,4-diazacycloalkanones:

In a manner analogous to that described hereinabove, an appropriately substituted piperidinyl may have its N-substituent cyclized in the non-catalytic ketoform reaction. For example, as illustrated in greater detail in example 2 hereinbelow, a 3-amino-1,3-dimethyl-butylamino- substituent is cyclized to a 1,4-diazacycloheptan-2-one.

Preparation of polysubstituted piperazinones:

The non-catalytic ketoform synthesis of this invention may be used to prepare polysubstituted piperazinones ("PSP") by reacting a N-(alkyl)-N'-(aminoalkyl/aryl/aralkyl/cycloalkyl)-1,"p"-alkanediamine, wherein "p" is the number of methylene C atoms (hereinafter "2AAD" for brevity).

PSPs with amine substituents are particularly desirable in the preparation of compounds in which the PSPs are distally linked to a triazine nucleus, as for example in compounds disclosed in copending application Ser. No. 350,536 filed Feb. 2, 1982. Such PSPs may be represented by the structure

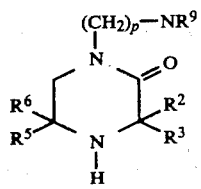

wherein, $R^9$ represents alkyl having from 1 to about 24 carbon atoms, cycloalkyl having from 5 to 7 carbon atoms, aralkyl having from 7 to about 20 carbon atoms, azaalkyl having from 1 to about 24 carbon atoms;

$R^2$, $R^3$, $R^5$ and $R^6$ have the same connotation as hereinbefore; and, p represents an integer in the range from 2 to about 10.

Analogous results are obtained when benzaldehyde, or p-methylbenzaldehyde is substituted for a ketone used in the foregoing reaction.

The non-catalytic ketoform synthesis may be used to introduce a substituent without resulting in the cyclization of the amine nucleophilic agent in several embodiments as follows:

Preparation of aminoacetamides:

Aminoacetamides with a wide range of substituents on the amine and amide N atoms may be carried over into the reaction product by a choice of the substituents. Similarly, a wide range of substitents may be introduced on the alpha-C atom by a choice of ketone or araldehyde. The reaction products obtained have the following structure

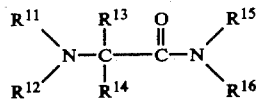

wherein, $R^{11}$, $R^{12}$, $R^{13}$, $R^{14}$, $R^{15}$ and $R^{16}$ independently represent hydrogen, aryl, alkyl having from 1 to about 24 carbon atoms wherein functional groups may be substituted with alkyl groups; hydroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; hydroxyalkyl ether or cyanoalkyl ether groups having from 4 to about 18 carbon atoms; alkenyl and aralkyl having from 7 to about 14 carbon atoms; alkylene having from 1 to about 7 carbon atoms; alkenylene having from 2 to about 10 carbon atoms; each substituent optionally containing a phosphite, ester or hindered phenol group, and each substituent in combination, $R^{13}$ with $R^{14}$, may form a ring containing from about 5 to about 9 ring atoms, which ring may also contain hetero atoms such as N, S or O, and optionally contain a keto, ester, amide, ether or thio group; except that each amine and amide N atom has at least one substituent.

Preparation of hydroxyethylaminoacetate:

The non-catalytic ketoform synthesis may be used to prepare an alkali metal hydroxyethylaminoacetate ("HEAA") which has N-adjacent C atoms on which there are a total of at least three substituents (hence "polysubstituted"), and one or both pairs of substituents on each N-adjacent C atom may be cyclized. The HEAA is represented by the following structure

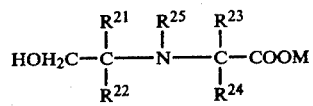

wherein, $R^{21}$, $R^{22}$, $R^{23}$ and $R^{24}$ are independently selected from the group consisting of hydrogen, aryl, alkyl having from 1 to about 24 carbon atoms, cycloalkyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 1 to about 18 carbon atoms;

$R^{21}$ and $R^{22}$ together, or $R^{23}$ and $R^{24}$ together, or each pair, may be cyclized forming a ring having from about 5 to about 8 carbon atoms;

except that not more than one of $R^{21}$, $R^{22}$, $R^{23}$, or $R^{24}$ may be hydrogen, and no more than three of $R^{21}$, $R^{22}$, $R^{23}$ and $R^{24}$ may be cyclic;

$R^{25}$ is selected from hydrogen, oxygen, hydroxyl and alkyl having from 1 to about 24 carbon atoms; and, M represents an alkali metal.

The process is simply and readily carried out, comprising, (a) contacting a 2,2'-substituted-2-amino ethanol represented by the following structure:

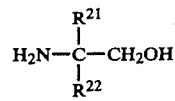

wherein $R^{21}$ and $R^{22}$ have the same connotation as hereinabove, and $R^{21}$ and $R^{22}$ may together be cyclized forming a ring having from about 5 to about 8 carbon atoms, with
(i) at least one molar equivalent of a haloform selected from the group consisting of chloroform and bromoform, and (ii) at least one molar equivalent of a carbonyl containing compound selected from the group consisting of monoketones and an araldehyde having from 7 to about 9 carbon atoms;

(b) maintaining a temperature in the range from about $-10°$ C. to about $30°$ C.; and, (c) adding at least one molar equivalent of an alkali metal hydroxide to form said alkali metal hydroxyethylaminoacetate.

Preparation of 'high' molecular weight aminoacetamides:

The non-catalytic ketoform synthesis will also yield reaction products in which there is no cyclization to a cycloalkanone, for example in the preparation of relatively high molecular weight substituted alpha-aminoacetamide represented by the structure

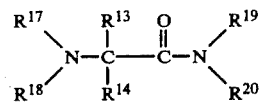

wherein, at least one of $R^{17}$, $R^{18}$, $R^{19}$ and $R^{20}$ substituents is alkylene imine having from 5 to 8 carbon atoms in which hydrogen atoms may be substituted with alkyl groups having from 1 to about 24 carbon atoms, and, when one substituent on either N atom is alkylene imine, the other substituent on that N atom represents hydrogen or said alkyl; and, $R^{13}$ and $R^{14}$ have the same connotation as hereinbefore, and each substituent, $R^{13}$ with $R^{14}$, $R^{17}$ with $R^{18}$, and $R^{19}$ with $R^{20}$, may in combination, one with another, form a ring containing from about 5 to about 9 ring atoms, which ring may also contain hetero atoms such as N, S, or O, and optionally contain a keto, ester, amide, ether or thio group; except that each amine and amide N atom has at least one substituent.

The following examples serve to illustrate the invention. Where not otherwise stated, parts are given as parts by weight and the temperatures in degrees centigrade.

EXAMPLE 1

Preparation of $N^1,N^4$-dimethyl-3,3-dimethyl-2-piperazinone having the structure:

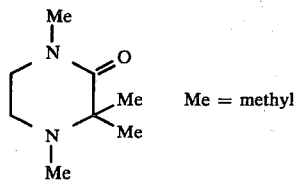

Me = methyl 8.8 g N,N'-dimethyl-ethylene diamine, 12.0 g CHCl$_3$, and 60.0 g acetone are placed in a 250 ml flask in an ice-bath, and to provide a homogeneous organic liquid phase. Then 40 ml conc NaOH (50% by wt) is dripped into the flask over about 30 mins. The reaction is allowed to proceed for about 5 hr and the reaction product is worked up as described hereinabove. Upon distillation the product is obtained. The foregoing structure of the compound is supported by IR, NMR, GC and mass spectrometer data.

EXAMPLE 2

Preparation of 3,3,5,5,7-pentamethyl-1-(2,2,6,6-tetramethyl-4-piperidinyl)-1,4-diazacycloheptan-2-one having the following structure:

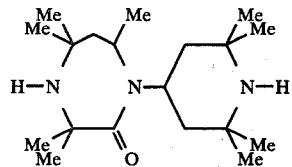

In a 250 ml three-necked flask were placed 9.8 grams (0.038 mol) of 4-(3-amino-1,3-dimethylbutylamino)-2,2,6,6,-tetramethylpiperidine, 9.2 g CHCl$_3$ and 25 g acetone. The flask is then immersed in an ice-bath and continuously stirred while 8.0 g of powdered NaOH is added to the contents of the flask the temperature of which is maintained below 25° C. The reaction is allowed to proceed overnight with constant agitation. Five hours after such addition the reaction is worked up by adding 150 ml CHCl$_3$ and 200 ml water. The water layer is extracted twice with CHCl$_3$ and combined with the original CHCl$_3$ layer. The combined chloroform from both layers is washed three times with 150 ml water. The CHCl$_3$ layer is then dried over anhydrous magnesium sulfate and concentrated to leave a yellow liquid. This yellow liquid is fractionated at reduced pressure. The fraction which boils at 130° C.–135° C. (at 0.95 mm Hg) is the reaction product which upon analysis, is found to have the structure written hereinabove.

EXAMPLE 3

Preparation of 1-[2-(2-butylamino)ethyl]-3,3,5,5-tetramethyl-2-piperazinone having the following structure:

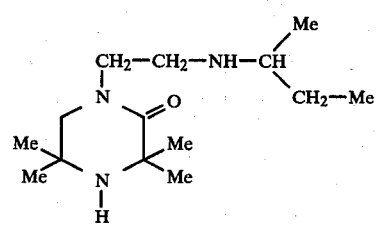

In a 3 liter three-necked flask were placed 131.1 g (0.7 mole) of N-(2-butyl)-N'-(2-amino-2-methylpropyl)-1,2-ethanediamine, 1 Kg (about 17 mols) of acetone, 100.2 g (0.84 mole) of chloroform, and cooled to about −10° C. after which was added 140 g of solid powdered sodium hydroxide slowly to the contents of the flask. After allowing the reaction to proceed overnight at about −4° C. the reaction temperature was gradually raised to 5° C. and maintained at this temperature for an additional 5 hours. After the usual work-up, the organic layer was stripped and distilled (b.p. 115°–120° C./0.25 mm Hg) to collect 71.5 g of very light straw colored syrup which was at lest 98% pure as shown by gas chromatography.

The structure written hereinabove was confirmed by proton nmr and FD spectroscopic data.

EXAMPLE 4

Preparation of alpha-phenyl, alpha-diethylaminodiethylacetamide having the following structure:

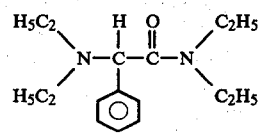

Into a 1 liter three-necked flask fitted with a reflux condenser is placed 14.6 g of diethylamine and 100 ml dichloromethane, followed by 25 g benzaldehyde (at least a two-fold excess is required), and 5.97 g chloroform. The reaction is initiated at room temperature 22° C. by the dropwise addition of 40 ml 50% NaOH aqueous solution over a period of several minutes. As the temperature of the reaction rose to the reflux temperature it began refluxing. The reaction mixture cooled to room temperature in a couple of hours and was allowed to continue to react at the lower temperature for a few hours after which the reaction mass was worked up. Typically this is done by extracting with dichloromethane, washing several times with water, drying and concentrating. Distillation yields the compound which upon analysis, is found to have the structure written hereinabove.

In an analogous manner, an aliphatic substituent, particularly lower alkyl, may be introduced by reaction of diethylamine with a three-fold excess of the corresponding (to the substituent desired) aliphatic ketone. A cyclic substituent may be introduced by reaction with a

11 cyclic ketone, for example, a cyclohexyl substituent with cyclohexanone.

EXAMPLE 5

Preparation of 2-(4-2,2,6,6-tetramethylpiperidine)-amino-2-pentamethylenediethylacetamide, having the following structure:

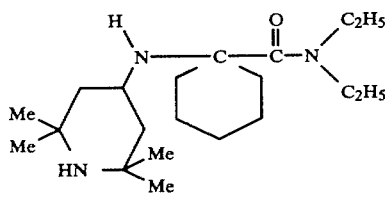

is prepared by taking 12.5 g 4-amino-2,2,6,6-tetramethylpiperidine having the structure

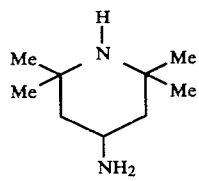

in a 1 liter three-necked flask fitted with a reflux condenser adding 22 g diethylamine and 100 ml dichloromethane, followed by about 30 g of cyclohexanone and 13 g of CHCl$_3$. To this reaction mixture is added about 40 ml of 50% NaOH, dropwise, over a period of about 5 minutes. The reaction is initiated at about 0° to about 5° C., and being exothermic, the temperature is controlled in this temperature range. The reaction mixture is held at about 10° C. overnight, while stirring, after which it was worked up. Typically the reaction mixture is worked up by extracting with dichloromethane, washing several times with water, drying and concentrating. The structure of the substituted diacetamide is confirmed by gas chromatographic (GC), infrared (IR), and nuclear magnetic resonance (nmr) analyses.

EXAMPLE 6

Preparation of sodium tetramethyl-hydroxyethylaminoacetate ("4M-HEAA") having the structure:

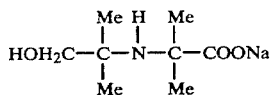

2-amino-2-methyl-1-propanol (0.6 mole), chloroform (0.8 mole), and acetone (10 mols) are placed in a three-necked flask cooled in a circulating ice bath so that the temperature is maintained in the range from about 0°–5° C. Aqueous sodium hydroxide (50% solution) is added dropwise into the contents of the flask while they are stirred. It is preferred to add at least four moles of NaOH for each mole of 2-amino-2-methyl-1-propanol, and a substantial excess over four equivalents is best. Also, in excess of one equivalent of chloroform is used, and nearly two equivalents is better. Stirring is continued overnight and the reaction mixture is filtered. The solid recovered is a mixture of 4M-HEAA and NaCl, but some of each may still be present in the filtrate. The organic phase is separated from the aqueous phase of the filtrate, and the ketone is recovered from the organic phase. If there is any 4M-HEAA in either the organic or aqueous phases, it may be recovered therefrom in any conventional manner. The solid is rinsed with methylene chloride to dissolve remaining organic phase on the solids which are then stirred into 300 ml methanol in which the 4M-HEAA dissolves but the NaCl does not. Crude 4M-HEAA is recovered from the methanol as a solid. Upon analysis, it is confirmed that the solid obtained is sodium tetramethylhydroxyethylaminoacetate.

In each of the foregoing examples, the ketone or araldehyde, is a carbonyl-containing compound which is a solvent for the amine nucleophilic agent (reactant compound), and if solubility is poor, a mutual solvent, not a primary alcohol, may be used. A primary alcohol is used only if it is to be a reactant, as taught hereinbefore. It is not essential that the reactant compound be soluble in the carbonyl-containing compound, but in view of mechanism of the reaction, it will now readily be evident that poorer solubility will result in unacceptably slow rates of reaction.

It will now also be evident that the rate of the reaction will best be controlled by the temperature of the reaction. Though higher temperatures of reaction give better reaction rates, the temperature of the reaction must be lower than that which will degrade the reaction product or the reactants, or which might form undesirable byproducts thus vitiating the directivity of the reaction. The temperature of the reaction is preferably controlled by controlling the rate of addition of base, and to a lesser extent, the amount of haloform used. The amount of base used, most preferably in solid form, and in slightly more than three times the molar eauivalents reauired for reaction with the amine nucleophilic agent, can readily be arrived at with a little experimentation, as may be the amount of haloform, most preferably chloroform, which is used in a slight excess (about 10–30%) over the molar amount required for producing the reaction product.

I claim:

1. A method for introducing an amine substituent into a carbonyl-containing compound comprising, contacting a primary or secondary amine reactant compound which is an amine nucleophilic agent with said carbonyl-containing compound selected from the group consisting of a saturated acyclic monoketone, a saturated cyclic monoketone and, benzaldehyde, optionally substituted with lower alkyl having from 1 to about 6 carbon atoms, in the absence of a phase transfer catalyst and a primary alcohol solvent, and in the presence of a base and sufficient haloform to provide a reaction product selected from the group consisting of a monoazacycloalkanone, diazacycloalkanone, alpha-aminoacetamide, and alpha-amino acetate;

said carbonyl-containing compound being present in an amount from about 2 to about 25 times greater than the molar amount required to react with said reactant compound;

maintaining the temperature during reaction below that which degrades said reactant compound; and, recovering said reaction product having said amine substituent.

2. The method of claim 1 wherein said base is an alkali metal hydroxide.

3. The method of claim 2 wherein said alkali metal hydroxide is present in a molar amount about three times greater than the molar amount of said reactant compound.

4. The method of claim 1 wherein said acyclic ketone is a lower alkyl ketone having from 2 to about 6 carbon atoms, and said cyclic ketone is a cycloalkanone having from 5 to about 8 ring carbon atoms.

5. The method of claim 1 wherein said primary or secondary amine having from 1 to about 24 carbon atoms wherein functional groups may be substituted with alkyl groups.

6. The method of claim 3 wherein said alkali metal hydroxide is in solid finely divided form.

7. A method for preparing a polysubstituted 2-keto-1,4-diazacycloalkane reaction product from an acyclic or cyclic 1,2-diamine or 1,3-diamine, comprising, contacting said 1,2-diamine or 1,3-diamine with a carbonyl-containing compound selected from the group consisting of a saturated acyclic monoketone, a saturated cyclic monoketone and, benzaldehyde, optionally substituted with lower alkyl having from 1 to about 6 carbon atoms, present in an amount from about 2 to about 25 times greater than the molar amount required to react with said diamine, in the absence of a phase transfer catalyst and a primary alcohol solvent, and in the presence of a base and sufficient haloform to provide said reaction product;

maintaining the temperature of reaction in the range from above about the freezing point of the reaction mass up to about the reflux temperature of said reaction mass; and, recovering said polysubstituted 2-keto-1,4-diazacycloalkanone.

8. The method of claim 6 wherein said diamine is an N-piperidinyl substituted diamine and said reaction product is a piperidinyl substituted 1,4-diaza-2-cycloalkanone.

9. The method of claim 6 wherein said diamine is a N-substituted-N'-substituted-N-alkanediamine and said reaction product is a polysubstituted piperazinone.

10. A method for preparing a polysubstituted alpha-aminoacetamide reaction product from an amino-piperidine comprising, contacting said amino-piperidine with a carbonyl-containing compound selected from the group consisting of a saturated acyclic monoketone, a saturated cyclic monoketone and, benzaldehyde, optionally substituted with lower alkyl having from 1 to about 6 carbon atoms, present in an amount from about 2 to about 25 times greater than the molar amount required to react with said amino-piperidine, in the absence of a phase transfer catalyst and a primary alcohol solvent, and in the presence of a base and sufficient haloform to provide said reaction product;

maintaining the temperature of reaction in the range from above about the freezing point of the reaction mass up to about the reflux temperature of said reaction mass; and, recovering said polysubstituted alpha-aminoacetamide.

11. A method for preparing a polysubstituted alkali metal hydroxy-aminoacetate reaction product from an amino-alkanol reactant, comprising, contacting said amino-alkanol with a carbonyl-containing compound selected from the group consisting of a saturated acyclic monoketone, a saturated cyclic monoketone and, benzaldehyde, optionally substituted with lower alkyl having from 1 to about 6 carbon atoms, present in an amount from about 2 to about 25 times greater than the molar amount required to react with said amino-alkanol, in the absence of a phase transfer catalyst and a primary alcohol solvent, and in the presence of a base and sufficient haloform to provide said reaction product;

maintaining the temperature of reaction in the range from above about the freezing point of the reaction mass up to about the reflux temperature of said reaction mass; and, recovering said polysubstituted alkali metal hydroxy-aminoacetate.

* * * * *